United States Patent [19]
Giuffre

[11] Patent Number: 6,042,548
[45] Date of Patent: Mar. 28, 2000

[54] VIRTUAL NEUROLOGICAL MONITOR AND METHOD

[75] Inventor: Kenneth A. Giuffre, Wyckoff, N.J.

[73] Assignee: Hypervigilant Technologies, Hohokus, N.J.

[21] Appl. No.: 08/970,738

[22] Filed: Nov. 14, 1997

[51] Int. Cl.[7] ............................................. A61B 5/0432
[52] U.S. Cl. ............................................................ 600/483
[58] Field of Search ............................................ 600/483

[56] References Cited

U.S. PATENT DOCUMENTS

| | | | |
|---|---|---|---|
| 4,230,125 | 10/1980 | Schneider | 600/483 |
| 4,495,950 | 1/1985 | Schneider | 600/483 |
| 4,688,577 | 8/1987 | Bro | 600/483 |
| 5,623,925 | 4/1997 | Swenson et al. | 600/483 |

*Primary Examiner*—William E. Kamm
*Attorney, Agent, or Firm*—McGlew and Tuttle, P.C.

[57] ABSTRACT

The monitor provides a means of registering and(or) predicting changes in brain and central nervous system activity by processing cardiovascular monitoring data and using pattern recognition by trained computing means to predict changes in the state of the central nervous system. Hence, a "virtual" neurological monitor is created where cardiovascular data are processed through the described means and a set of real-time neurological state predictions are made.

20 Claims, 6 Drawing Sheets

VIRTUAL NEUROLOGICAL MONITOR AND METHOD

BACKGROUND OF THE INVENTION

1. Field of the Invention

The present invention relates to neurophysiological monitoring systems that provide clinical and(or) research data on the relationship(s) between changes taking place in the central nervous system during stress, surgery, anesthesia, and other conditions resulting in dynamic brain state changes; and resulting changes seen in the autonomic nervous system and the cardiovascular system. Such systems, when noninvasive, provide less risk to subjects while guiding management, diagnosis, and treatment and(or) alerting observers to changes like awareness under anesthesia, brain ischemia, pain, and severe stress.

Since neurophysiological monitoring equipment per se adds to the complexity of setup, increases the demands on the operator, raises the cost of care, and if used improperly, adds to the risk of mistaken interpretation, a system that can predict brain states using already implemented cardiovascular monitoring modalities will allow for such predictive capabilities while minimizing risk, cost, and added complexity of such a setup.

2. Description of the Prior Art

Neurological and cardiovascular physiological monitoring systems currently in use utilize a number of methods to provide observers with information on the functional states of the central nervous system, autonomic nervous system, and the cardiovascular system.

Invasive cardiovascular dynamic measurements in use include analysis of peripheral arterial pulses, pressures taken from catheters placed in the great veins, the heart chambers, the pulmonary arterial bed, and the pulmonary venous bed; continuous and intermittent thermodilutional methods of cardiac output assessment; radiotracer scanning; and continuous fiberoptic oximetric assessment of central mixed venous hemoglobin oxygen saturation.

Noninvasive cardiovascular and neurological monitoring systems employ electrophysiological measurements from the skin based on native bioelectric impulses (as in standard electroencephalography (EEG), processed EEG, standard electrocardiography (ECG), and processed ECG) or resulting from programmed stimuli to the skin or sensory organs as in somatosensory evoked potentials (SSEP), brainstem audio evoked response (BAER), visual evoked potentials (VEP), motor evoked potentials (MEP), and facial electromyography (FACE); or from programmed current passed through the body to obtain an index of bioimpedance as a means of predicting cardiovascular dynamics.

Other noninvasive systems employ plethysmographic or doppler techniques to provide a pulse waveform for analysis or utilize ultrasound in the form of echocardiography imaging, simple surface or esophageal Doppler analysis, or detect sound as in phonocardiography.

Recently, a great deal of research has been conducted into mathematical models to predict the cardiac output, left ventricle filling and ejection volumes of the heart, and stroke work of the heart; based on changes in the bioelectric impedance of the thorax to varying weak alternating electrical currents. This technique, known as thoracic bioimpedance, has been shown to accurately and noninvasively predict changes in cardiovascular dynamics in response to various stimuli including hemorrhage, shock, stress, and anesthesia (U.S. Pat. No. 5,309,917). Biboulet et. al. (Br.J.Anesth. 1996;76(1):81–84) for example, using the technique of thoracic bioimpedance, has shown that patients exposed to blood dilution have a much different cardiovascular response when anesthetized during said dilution. This supports the concept that bioimpedance-based cardiovascular analysis is sensitive to cardiovascular changes that occur during the transition from the awake to the anesthetized state. Thus far, bioimpedance per se has not been used as a gauge to measure level of consciousness by itself nor in combination with direct cerebral monitoring as with evoked potentials or EEG. Since subtle patterns of change in cardiovascular patterns are more telling with respect to changes in brain states, and absolute numbers less important, Giuffre and Anzano have recently proposed an improvement in existing bioimpedance modeling involving the use of a pulse or doppler plethysmographic signal from the heart itself or a peripheral artery to more accurately estimate systolic ejection time in combination with traditional bioimpedance cardiovascular modeling algorithms (Giuffre, Anzano, U. S. Patent filing November, 1977).

Several authors have also recently shown that differing levels of consciousness, stress, and anesthesia result in changes in the normal heart rate variability that occurs in response to breathing and which has been termed cardiac vagal tone (Billman et. al., Heart Circ Physiol, 1990; 27:H896–H902) because the vagus nerve of the parasympathetic autonomic nervous system is thought to mediate these heart rate changes, also described by Porges (Pediatrics 1992, 90:498–504) and which forms the basis for biophysical analysis in U.S. Pat. No. 4,510,944 and in Jaffe et. al. (J Clin Monit 1994, 10(1):45–48). Anesthetic depth has been shown to affect vagal tone (Ireland et. al., Br J Anesth 1996, 76(5):657–62), (Latson et. el., J Clin Anesth 1992;4(4):265–76), (Alkire et. al., Anesthesiology 1997; 87(3A);A175). These methods utilize ECG or pulse measurements and thus far have not incorporated EEG-trained classification and prediction computer models into their data collection and processing.

Other methods that have attempted to reliably measure brain activity as a function of level-of-consciousness, anesthetic depth and(or) state of alertness include sensors measuring microexpression changes in the face (U.S. Pat. No. 5,195,531)(Struys et. al., Anesthesiology 1997; 87(3A):A9), heart rate response to ocular compression (Shapiro et. al., Psychophysiology 1996;33(1):54–62), contractile response of the lower esophagus (Maccioli et. al., J Clin Monit 1988;4(4):247–55), and the H-reflex measuring amplitude and latency of spinal reflex arc at the tibial nerve (Magladery et. al., Bull Johns Hopkins Hosp 1951;88:499) and other reflex arc responses (Chabal et. al., Anesthesiology 1989;70:226–29). Electrical stimulation has been shown to even affect levels of central nervous system chemical mediators of mood and pain sensation. Low frequency peripheral electrical stimulation raises brain levels of endogenous opiates and is antagonized by opiate antagonists (Chiang, Scientia Sinia 1973;16:210–217, and Pomerantz, Basis of Acupuncture, Springer Verlag 1991:250–260). Higher frequency peripheral electrical stimulation raises brain amines like serotonin (Han, Scientia Sinia 1979; 22:91–104 and Lichtman et. al. Behavioral Neuroscience 1991; 105(5):687–98). None of these brain responses to various modes of stimulation have been correlated with direct neurological monitoring data in combination with a trained computer classification and prediction model. A neural net was used in comparing hemodynamic responses to electroencephalography and facial myography (Watt et. al., Anesthesiology 1995;83(3A):A32, and Lang et. al., Anesthesiology 1994;81(3A):A197) but no attempt was made at using the hemodynamic data to back-predict the neurophysiological data.

Beyond simple, wave processed (Billard et. al., Anesthesiology 1993; 79(3A):A174), and bispectral index electroencephalography (U.S. Pat. No. 5,010,891), (Rosow et. al., Anesth Clin of NA: Annual of Anes Pharm 1998;2:89–107), (Billard et. al., Anesthesiology 1996; 85(3A):A32); other variations have been utilized to measure anesthetic depth and level of consciousness. In U.S. Pat. No. 4,869,264, the EEG response to infrared light passed through closed eyelids is utilized. Even further involvement of the body sensory means via stimulation are demonstrated in U.S. Pat. No. 4,570,640 where the body surface is stimulated, and in U.S. Pat. No. 4,201,224 where statistical Z transformations are used to process multimodal stimulation response as measured by EEG, ECG, and evoked potentials. Though this method uses a statistical predictive model, it does not attempt to create data prediction in the absence of neurological monitoring. In the method described by Muthuswamy et. al. (J Clin Monitoring 1996; 12:353–364), measurement of end tidal expired carbon dioxide is utilized in combination with processed EEG and a predictive computer algorithm. None however, have specifically combined their specific method of physiologic monitoring with neurologic monitor output to train a classification/prediction model for predicting states of central nervous system activity as a function of said physiological monitoring in the absence of neurologic monitor data.

Evoked potential monitoring has also been utilized as a measure of level of consciousness (Doi et. al., Br J Anes 1997; 78:180–84) as well as positron-emission tomography (PET) scanning (Anesthesiology 1996;85(3A):A9).

Various computer techniques have been employed in the creation of classification/prediction models for management of biophysical monitoring data. Neural network programming algorithms have been shown to be effective for recognizing patterns in biophysical monitoring modes (Baxt WG, Lancet 1995;346:1135–38). Kloppel describes the use of neural networks in EEG analysis (Neuropsychobiology 1994;29:33–38) along with Jando et. al. (Electroencephalography and Clin Neurophys 1993;86:100–109). Neural networks in EEG analysis have even been used in analyzing stages of sleep (Schaltenbrand et. al., Sleep 1996; 19(1):26–35). Neural networks have also been utilized in pattern recognition of neurological evoked potential signals (Laskaris et. al., Electroencephalography and Clin Neurophys 1997;104:151–56).

Statistical methods have also been used as previously mentioned in the citation of U.S. Pat. No. 4,570,640 and in other modes of monitoring including neonatal monitoring of heart rate variability and audiology testing (both cited by Abtech Corp., Charlottesville, Va., 1995).

Newer software methods combine statistical analysis with neural net training (e.g. Model Quest software, Abtech Corp., Charlottesville, Va., 1996) or neural net training with genetic algorithms for inducing changes in neural net configuration to auto-optimize the model during training (e.g. Neuroshell Easy Predictor; Neuroshell Easy Classifier; both by Ward Systems Group, Frederick, Md., 1997).

None of the above methods combine specific methods of physiological assessment with EEG-based training of neural networks to allow prediction and assessment of either state of anesthetic depth or state of consciousness by using said EEG-trained neural net to predict the state of the central nervous system as a function of the output of said physiological assessment and without the input from an EEG or other brain-based monitoring system.

SUMMARY AND OBJECTS OF THE INVENTION

According to the invention, real time neurophysiological diagnostic apparatus is provided along with a method for evaluating changes in cardiovascular dynamics and utilizing a classification and prediction computing means (e.g. statistical program, neural network, genetic algorithm, or hard-wired parallel distributed processing computer) to estimate brain activity like general arousal and autonomic neural activity as a function of a training period in which data produced by one or several cardiovascular monitoring means is coupled with direct neurophysiological monitor data (EEG, evoked potentials, processed EEG et. al.; refer to claims). After such a training period, the data from the noninvasive cardiovascular monitoring means is interpreted via the trained neural net or other parallel system or self-teaching system without being coupled to the neurophysiological monitor means. Hence, the result is a noninvasive cardiovascular monitor which, using a trained pattern recognition system, estimates the neurophysiological state of the subject. Hence, the result is a cardiovascular monitoring system which, using a trained pattern recognition system, estimates the neurophysiologic state of the subject thereby acting as a "virtual" brain monitor. In the preferred embodiment, noninvasive cardiovascular monitor means capable of registering such changes in the cardiovascular system in response to central nervous system and(or) autonomic system changes include thoracic bioimpedance, electrocardiography, and heart rate variability. Since a large body of biomedical research has demonstrated a direct relationship between changes in psychological states, states of arousal, states of stress, and states of consciousness with corresponding changes in the behavior of the cardiovascular system, the disclosed system can estimate brain and central nervous system activity.

The self-teaching computer can comprise a neural net software with or without genetic training algorithms (including but not limited to simple multilayer single connection nets, recurrent nets with connections to previous layers with various amounts of dampening in these back connections (Jordan-Elman nets), multiple hidden layers with differing characteristics (Ward nets), recurrent nets where each layer is back-connected to every previous layer (jump connection nets), unsupervised classification net models (Kohonen nets), supervised classification net models (probabilistic nets), nets involving grouped data handling (polynomial and regression nets), and general genetic regression neural networks (GRNN)), a neural net chip with accompanying software and(or) a parallel processor; alone and(or) in combination with standard statistical evaluation means. Such a trained computing means acts in real-time though training can occur at slower rate to allow for specific human operator data and program manipulation, and(or) incorporation of an additional genetic-type algorithm or other optimization system(s) to incrementally perturb the system and(or) change models until data management is optimal.

In one particular embodiment, a neural net software program is fed derived information from a thoracic bioimpedance monitoring system whose processing of systolic ejection time is improved by the use of pulse plethysmography (Giuffre', Anzano, U.S. Patent filing November 1997); is coupled with a bispectral processed EEG system via a training protocol with data being entered through a variety of state changes. The resultant trained neural net software model then acting free of electroencephalographic input, evaluates the improved bioimpedance-measured cardiovascular state and produces an estimated neurophysiologic profile of the subject being monitored.

In the described embodiment, various neural net models can be manipulated and tested for optimal performance. Neural net architectures uses can include simple nets where each input is connected to each node in a single or multiple hidden layers with various methods of connection, weighting, dampening, and learning as described herein.

The disclosed method provides a simple, noninvasive means for determining the level of arousal or depth or anesthesia of a subject, or other brain state, without requiring the use of electroencephalography or other neurophysiologic monitoring means, and hence, eliminating the need for associated electrodes attached to the head and other neural structures, the attendant cost, and the associated demands of attention and time on support staff. Instead, a real-time neural network that has been trained to associate patterns of cardiovascular biodynamics with electroencephalographic patterns, provides an estimate of the current neurophysiologic state of the patient thereby simulating the output of a neurophysiologic monitoring means, i.e., a "virtual" brain-state monitoring means.

It is an object of the invention to allow for monitoring of neurological changes without requiring the use of elaborate neural monitoring systems and their associated electrodes. Besides adding convenience and decreasing cost to the monitoring procedure, it makes the setup less complicated and hence, less error-prone. Furthermore, in situations where placement of electrodes on the head and other neural structures is impractical or difficult; states of arousal, sleep, stress, anesthesia, and brain insults like ischemia, can still be monitored.

It is a further object of the invention to make use singly or in combination, one or more cardiovascular monitoring means. Such means can include thoracic bioimpedance, electrocardiography, analysis of heart rate variability, invasive central cardiac and pulmonary arterial monitoring, pulse waveform analysis, et. al.

In embodiments where thoracic bioimpedance is utilized, standard chest bioimpedance electrodes can be used or, to simplify setup and operation while decreasing cost, a limited method of bioimpedance current and pickup can be coupled directly to standard ECG electrodes. Such data while possibly not providing optimal absolute cardiovascular baseline numbers, will register changes in bioimpedance-based cardiovascular parameters, changes being more important at providing correlation with changes in the central nervous system state than the absolute cardiovascular numbers per se. Furthermore, data provided by pulse plethysmography can refine said thoracic bioimpedance calculation models by providing for enhanced estimation of cardiac systolic ejection time (Giuffre', Anzano, U.S. patent filing November 1997).

According to one embodiment of the invention, level of consciousness of patients can be assessed by training the self-teaching computer to recognize such states through coupling said cardiovascular data to simple or processed EEG data. Other states and state changes that the self-teaching computer can be trained in include non-anesthetic sleep states for sleep monitoring; stress levels as a means of biofeedback, meditation, or lie detection; and brain ischemia or reduced cerebral bloodflow as might occur during vascular surgery, shock, or during high g-force maneuvers in aircraft or spaceflight means.

According to another embodiment of the invention, depth of anesthesia can be measured using similar methods and incorporating warning means to alert the operator of impending changes such as awakening or conversely, reaching dangerous levels of anesthetic depth. Similarly, warning means can be coupled to systems described to warn operators of impending loss of consciousness as might occur during high g-force flight maneuvers or impending brain ischemia with vascular occlusion during surgery.

It is a further object of the invention to help monitor non-anesthetic drug-induced brain changes as produced from drug overdose, drug abuse, or drug therapy as in intravenous magnesium therapy for toxemic pregnant patients where magnesium acts as a brain depressant. Similarly, brain states accompanying alcohol withdrawal and drug withdrawal during rehabilitation therapy can be monitored, as well as the level of brain impairment that accompanies alcohol or drug intoxication.

It is a further object of the invention to provide easy monitoring of seizure activity as is produced during psychiatric electroconvulsive therapy.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS In the drawings.

DESCRIPTION OF THE PREFERRED EMBODIMENT

Figure 1A:
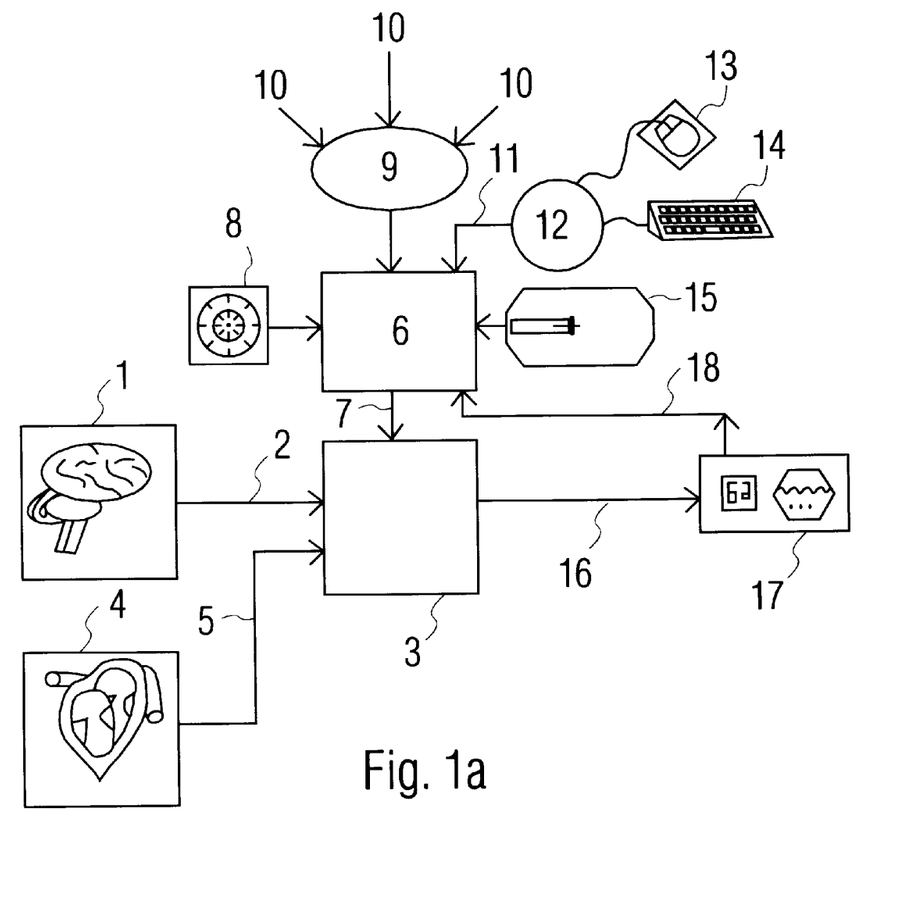
FIG. 1a is a block diagram depicting the relationship between cardiovascular monitor means, brain monitor means, and event data collection means, all feeding data into computer classification and prediction means which is in the training mode.

Referring to the drawings in particular, FIG. 1a depicts a block diagram in which the brain of the subject is monitored via brain monitoring means 1. The brain monitoring data 2 is transferred to computer classification and prediction means 3 which is in the training mode. Simultaneously, cardiovascular data 5 is transferred from cardiovascular monitoring means 4 to computer classification and prediction means 3. To further enhance training, event parameter organizer 6 transfers event data 7 that is being recorded simultaneously, to the computer means 3 in said training mode. Event organizer 6 receives data from various sources including specific training software delivery means 15, miscellaneous event recorder 9 recording miscellaneous events 10, human interface organizer means 12 receiving data from mouse-type data input device 13, and keyboard type input device 14. Further embodiments could include voice and pen input to 12 as well, which could also convey human input data via 11 to event organizer 6 and ultimately via 7 to computer classification and prediction means 3. Events, in order to be properly organized with cardiovascular input 5 and brain input 2, are marked for time via timing means 8. Processed data from the computer means 3 is sent via 16 to virtual neuro monitor 17 which displays predicted brain monitoring data resulting from computer means 3 to the operator in a variety of forms including two dimensional moving graphic and simple numerical display(s) on virtual brain monitor 17. This output can be fed back to the event organizer means 6 for the purposes of enhancing training of the computer means 3.

The event means may be one of a variety of devices or a supply of data which is useful for the training phase or for the continued training of the monitoring system. Although a training period or phase is refered to herein, this may be ongoing or continuous. At least some initial training phase is need prior to use of the system as a monitor. Event means that are useful include one or more of: an expired gas concentration evaluation system for obtaining expired gas concentration data; a drug infusion device providing drug infusion data; input gas concentration regulation means providing input gas concentration data; means for supplying data derived from spreadsheet type data depositories; human operator input based on subjective and(or) objective evaluation of the subject being monitored; expired ethanol analysis; magnesium levels monitoring means for obtaining magnesium therapy monitoring data; specific drug or alcohol blood level monitoring means to provide drug/alchohol blood level data; a standard skin galvanic resistance lie detector for providing galvaning lie detector resistance data; a meditation state source data indicating achieved states of meditation; means for monitoring specific events during surgery and providing surgery event data; g-force measurement means for providing g-force data within an aircraft, spacecraft, and(or) flight simulator; and means for providing psychometric performance data based on answers to questions and(or) performance of specific tasks.

The cardiovascular monitoring means may be one or more of: a thoracic bioimpedance monitoring means; a modified thoracic bioimpedance monitoring means that concomitantly utilizes electrodes positioned on the subject and used for electrocardiographic analysis; a heart rate variability real-time time series analysis device; a electrocardiographic morphology analysis device operating in real time and producing interpretive data; a electrocardiographic real-time Fourier-type spectral waveform analysis device with or without producing interpretive data; a real-time electrocardiographic interpretive arrhythmia waveform analysis device; a real-time interpretive electrocardiographic ischemic waveform analysis device; a noninvasive plethysmographic or doppler peripheral pulse waveform data gathering device; invasive waveform and(or) pressure data means gathering data from the systemic arterial system, pulmonary arterial system, occluded pulmonary arterial system, and cardiac chambers; a device for providing continuous thermodilution cardiac output data from invasive catheter(s); means for providing continuous mixed venous oxygen hemoglobin saturation data; means for supplying echocardiographic data in one, two, or three dimensions.

After a period of training and testing of the resulting model, the system is run without input from event organizer 6, and brain monitor 1. The resulting trained system 3, depicted in FIG. 1b, where only cardiovascular data 5 is provided via cardiovascular monitoring means 4; makes a prediction via 16 to virtual neuro monitor 17 that simulates the situation as if actual brain monitoring were in place. This apparent but absent "virtual" brain monitor 19 input 20 is depicted with stippled lines and represents the virtual input that produces output 16 by way of cardiovascular monitor means 4 passing data 5 to computer classification and prediction means 3, now trained to predict the output that would appear on display means 17 as if real brain monitor means 1 were present. This ability of computer classification and prediction means 3 to make such predictions is based on the training provided as was discussed with reference to FIG. 1a.

Figure 2:
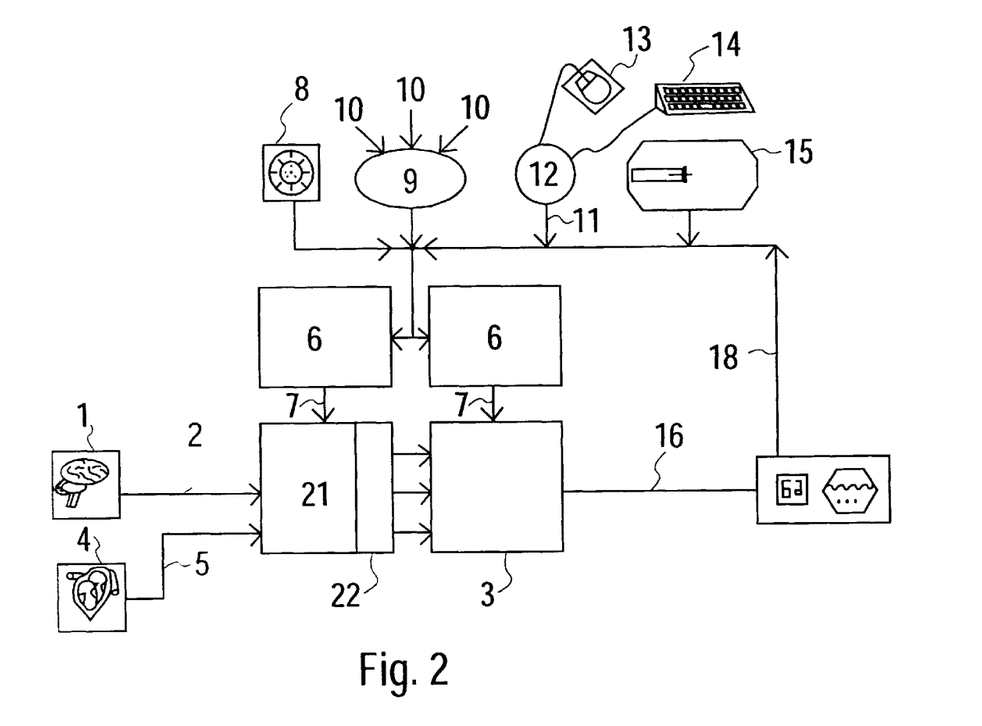
FIG. 2 is a block diagram depicting the computer classification and prediction means in the training mode as depicted in FIG. 1a except the data is stored and released to the computer means at a slower timed rate for less-than-real-time processing and training. Here the computer classification and prediction means is in the training mode.

Since some of the data manipulation required for adequate training of computer classification and prediction means 3 may require considerably more time than allowable during real-time processing, FIG. 2 depicts a method by which real-time data is stored in input data storage means 21 and given a time label by timer means 22. Event organizer 6 can provide input to data storage means 21 or provide input directly into computer classification and prediction means 3. Timer means 22 also allows release of stored brain, cardiovascular, and event data to computer means 3 for training and training manipulation in a mode slower than real time. This method is particularly useful for allowing human operator input 11 to act on otherwise normally rapidly acquired input data.

Figure 1B:
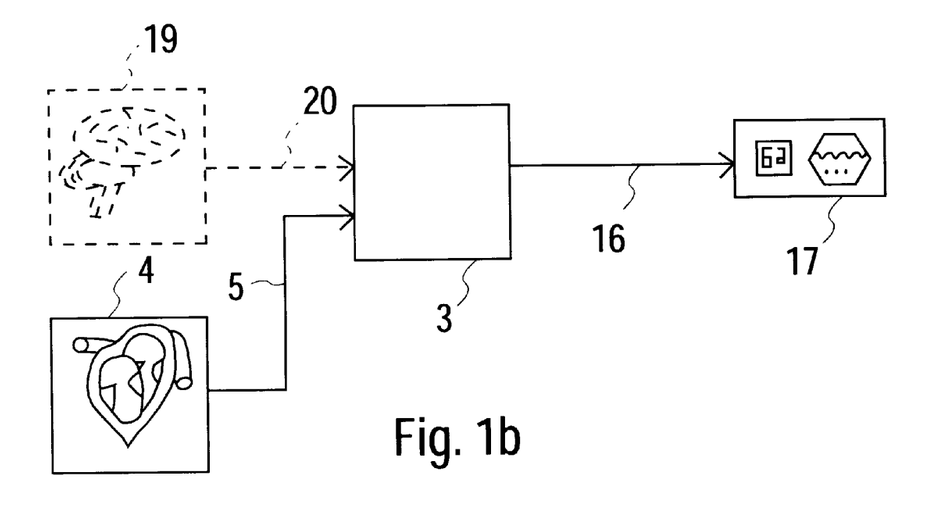
FIG. 1b is a block diagram depicting the relationship between the cardiovascular monitor means, the computer classification and prediction means, and the output means which portrays data resulting from prediction based on the trained system and resulting in an output simulating that which would be produced by brain monitor means alone, hence a "virtual" brain monitor means. Here the computer classification and prediction means has been fully or partially trained.

In situations where it is feasible to use brain monitoring means 1 in real-time for actual subject monitoring even when computer classification and prediction means 3 is already trained to make predictions from cardiovascular data input 5 as described via FIG. 1a, FIG. 1b, and FIG. 2; the computer means 3 can act as an aid to detect and replace artifact that would otherwise interfere with adequate interpretation of a signal based on brain monitor data 5 alone.

Figure 3:
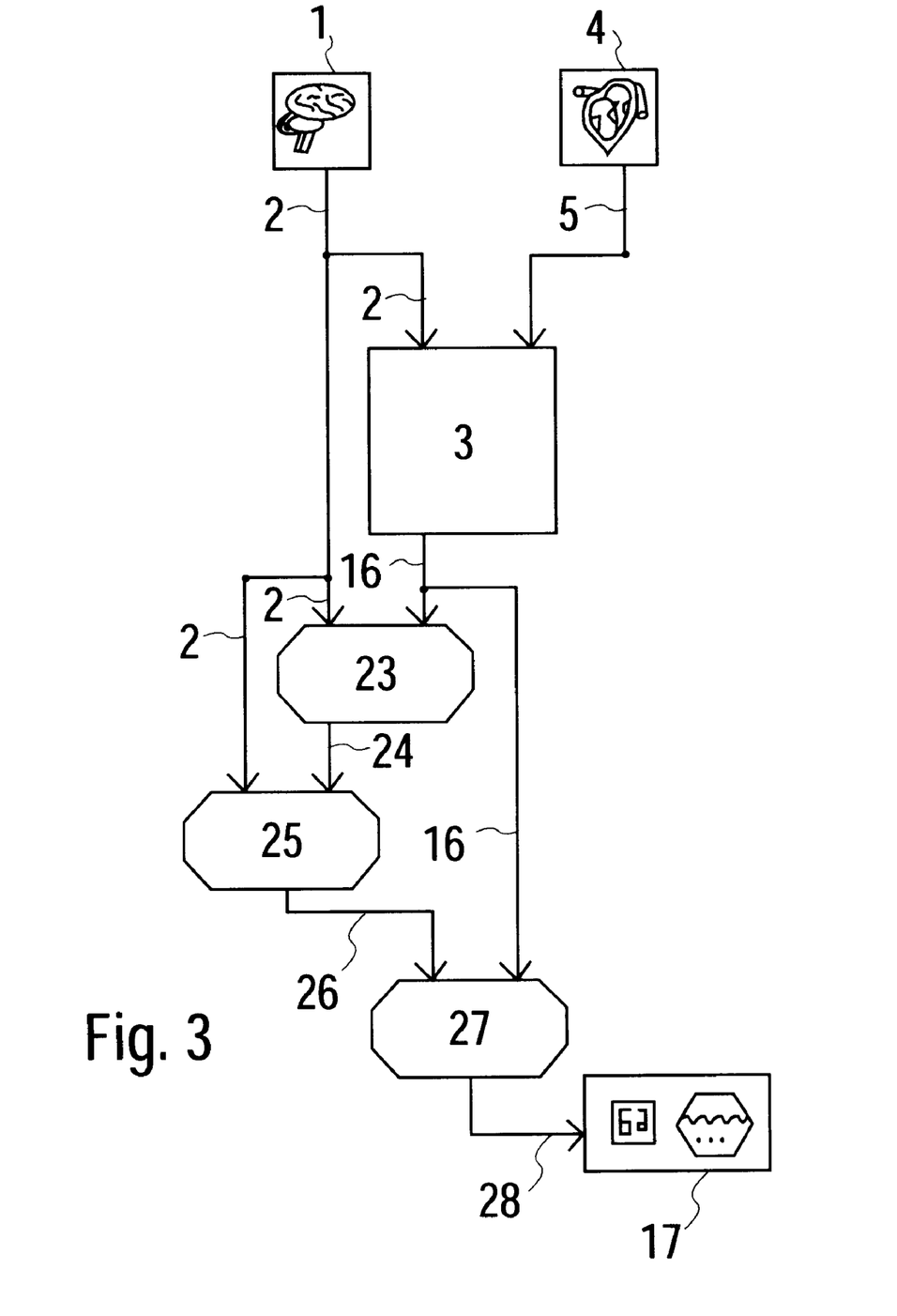
FIG. 3 is a block diagram depicting a method by which the trained computer classification and prediction means can use data from cardiovascular monitor means to create a simulated brain monitor means signal which it compares with an actual brain monitor means signal, and using a series of comparator means, constructs a hybrid signal with decreased artifact.

In the artifact detection and replacement means outlined in block diagram in FIG. 3, computer classification and prediction means 3 is already in a trained state to act as a "virtual" brain monitor by making predictions solely based on cardiovascular data 5. This predicted "virtual" brain data is transferred via 16 to comparators 23 and 27. In comparator means 23, "virtual" brain data derived from cardiovascular data 5 via trained computer means 3 is combined with actual brain data 2 coming from brain monitor means 1. Comparator means 23 specifically compares the signals and the resulting signal 24 comprises a flat signal interspersed with pieces labeled as artifact that were identified by the comparator means based on identifying signal patterns from real brain input data 2, that in their actuality, differ significantly from the predicted signal patterns 16.

The artifact signal 24 is then fed to comparator means 25 and compared to actual brain monitor signal 2, said comparator means 25 designed to splice real signal with artifact areas deleted, resulting in signal 26 which comprises a real signal reproduction with gaps where artifact has been identified.

The real brain monitor signal with gaps 26 is fed to comparator means 27 which fills these gaps with virtual brain monitor signal 16 predicted by computer means 3 from cardiovascular input 5. The result is spliced signal 28 comprising real brain data signal 2 with areas of identified artifact replaced by "virtual" predicted data signal 16. This resulting signal is fed to display means 17 for use by the operator.

Figure 4A:
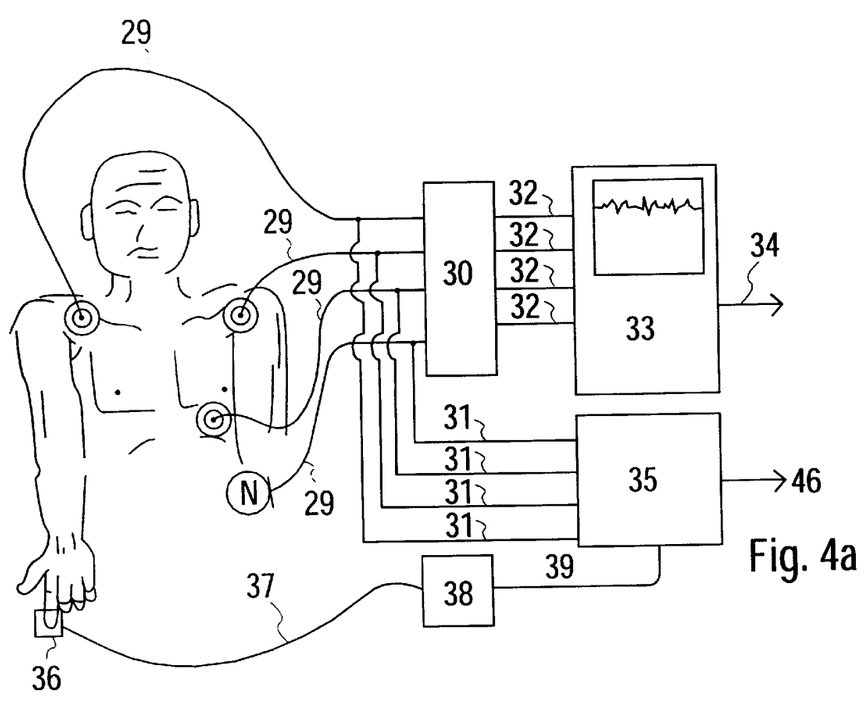
FIG. 4a depicts a subject undergoing cardiovascular monitoring via the preferred embodiment whereby a bioimpedance cardiovascular monitoring means acts through the leads of an electrocardiography monitor whose signal is processed by a low pass filter so as not to interfere with the ECG signal. The bioimpedance monitor is specifically configured such that a pulse plethysmographic means connected to a digit on the subject aids in the processing of the bioimpedance signal (method described by Giuffre, Anzano, U.S. patent filing November 1997)

In the preferred embodiment, the cardiovascular monitoring means 4 comprises a combination of electrocardiographic, bioimpedance, and pulse plethysmographic data as depicted in FIG. 4a. In this version of the invention, 3–4 or more electrocardiographic monitoring leads 29 (1,2,3, . . . N) in addition to supplying data to electrocardiographic monitor means 33 and to computer means 3 via 34; are also used to obtain data on thoracic bioimpedance. Here, low pass filter 30 allows ECG signals to pass but prevents any input/interference by higher frequency bioimpedance signals. These signals are conveyed via 3–4 or more electrical conduits 31 (1,2,3, . . . N) to bioimpedance apparatus 35 which in combination with data from pulse plethysmograph 36 data 37 to pulse plethysmograph signal processor 38, benefits from signal 39 which provides an additional estimate of systolic ejection time in accordance with the Giuffre Anzano method described. The resulting bioimpedance cardiovascular parameter data 46 produced are transferred to computing means 3. Bioimpedance means 35 also comprises an optimization means to detect and determine the optimal combination of leads 31 (1,2,3, . . . N) to input said bioimpedance signal and detect it from various input and output lead 29 arrangements.

Figure 4B:
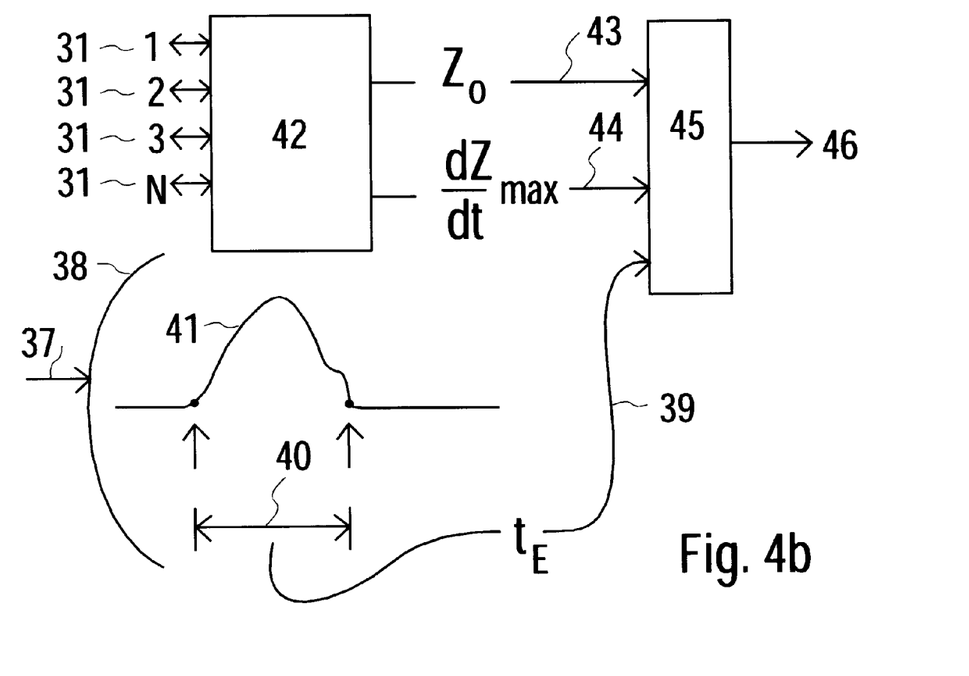
FIG. 4b depicts the bioimpedance cardiovascular monitoring means in block format demonstrating one method by which different methods of cardiovascular monitoring can be combined, specifically in this embodiment, said Giuffre Anzano method by which pulse plethysmographic signal is utilized to obtain systolic ejection time and multiplied with bioimpedance baseline impedance and impedance derivative maximum to produce accurate cardiovascular measurements.

The above referenced Giuffre Anzano method by which pulse plethysmographic data 39 can assist bioimpedance apparatus 35 in producing more accurate cardiovascular parameter data as described is outlined briefly in FIG. 4b. Plethysmographic pulse signal 37 is fed to plethysmograph signal processor 38 where major deflections from baseline from plethysmographic waveform 41 are detected and measured, producing systolic ejection time estimate 40. Estimate 40 is sent as data 39 to multiplier 45 within bioimpedance apparatus 35 which is fed bioimpedance data from 3–4 or more leads 1,2,3, . . . N via signal processor and differentiation means 42 also located within bioimpedance means 35. Two resulting signals include baseline thoracic impedance 43 and maximum rate of change in bioimpedance 44. These signals multiplied produce cardiovascular data estimate 46, fed to computer means 3.

The above description of the diagrams and the preferred embodiment are one possible method of carrying out the purposes outlined herein and as a means for explaining some of the principles claimed. The various features of novelty which characterize the invention are pointed out with particularity in the claims annexed to and forming a part of this disclosure.

While specific embodiments of the invention have been shown and described in detail to illustrate the application of the principles of the invention, it will be understood that the invention may be embodied otherwise without departing from such principles.

What is claimed is:

1. A monitoring system, comprising:

a cardiovascular monitoring means for providing cardiovascular data;

brain monitoring means for providing brain monitoring data;

classification and prediction computing means for processing said cardiovascular data in a real-time fashion, said computing means comprising a trainable system having a training phase comprising analysis of said cardiovascular data said brain monitoring data collected from a same patient or precorelated data to provide a trained state, said classification and prediction computing means, when in said trained state providing brain monitoring prediction data on the basis of said cardiovascular monitoring data without the use of said brain monitoring data.

2. The monitoring system in accordance with claim 1, wherein said computing means training phase may occur at a slower rate than a real time processing rate to allow for input from one of a human operator and additional computer analytical tools to optimize said training phase.

3. The monitoring system in accordance with claim 1, further comprising event data means for providing event data, wherein said computing means training phase further includes analysis of said event data with said analysis of said cardiovascular data said brain monitoring data.

4. The monitoring system in accordance with claim 1, wherein said computing means in said trained state feeds back to a said brain monitoring means to improve noise artifact recognition by comparing predicted brain monitor output data to actual brain monitor output data.

5. The monitoring system in accordance with claim 3, wherein said event data means includes one or more of:

an expired gas concentration evaluation system for obtaining expired gas concentration data;

a drug infusion device providing drug infusion data;

input gas concentration regulation means providing input gas concentration data;

means for supplying data derived from spreadsheet type data depositories;

human operator input based on subjective and(or) objective evaluation of the subject being monitored;

expired ethanol analysis;

magnesium levels monitoring means for obtaining magnesium therapy monitoring data;

specific drug or alcohol blood level monitoring means to provide drug/alchohol blood level data;

a standard skin galvanic resistance lie detector for providing galvaning lie detector resistance data;

a meditation state source data indicating achieved states of meditation;

means for monitoring specific events during surgery and providing surgery event data;

g-force measurement means for providing g-force data within an aircraft, spacecraft, and(or) flight simulator; and means for providing psychometric performance data based on answers to questions and(or) performance of specific tasks.

6. The monitoring system in accordance with claim 1, wherein said training phase can continue beyond an initial training period wherein said brain monitoring prediction data is provided on the basis of said cardiovascular monitoring data without the use of said brain monitoring data after said initial training period.

7. The monitoring system in accordance with claim 1, wherein said cardiovascular monitoring means comprises one or more of:

a thoracic bioimpedance monitoring means;

a modified thoracic bioimpedance monitoring means that concomitantly utilizes electrodes positioned on the subject and used for electrocardiographic analysis;

a heart rate variability real-time series analysis device;

a electrocardiographic morphology analysis device operating in real time and producing interpretive data;

a electrocardiographic real-time Fourier-type spectral waveform analysis device with or without producing interpretive data;

a real-time electrocardiographic interpretive arrhythmia waveform analysis device;

a real-time interpretive electrocardiographic ischemic waveform analysis device;

a noninvasive plethysmographic or doppler peripheral pulse waveform data gathering device;

invasive waveform and(or) pressure data means gathering data from the systemic arterial system, pulmonary arterial system, occluded pulmonary arterial system, and cardiac chambers;

a device for providing continuous thermodilution cardiac output data from invasive catheter(s);

means for providing continuous mixed venous oxygen hemoglobin saturation data; and means for supplying echocardiographic data in one, two, or three dimensions.

8. The monitoring system in accordance with claim 1, wherein said brain monitoring means comprises one or more of:

a full multiple lead electroencephalography device;

full multiple lead electroencephalography device with individual Fourier wave analysis in real time of every channel;

a processed EEG resulting in data comprising complex graphical or numeric output, simplified graphical or numeric output, and(or) a simple scaled numerical value correlating with general cerebral unilateral or bilateral cortical activity;

an evoked potential measurement means from somatosensory evoked potentials, brainstem auditory evoked potentials, visual evoked potentials, and(or) motor evoked potentials;

a positron emission tomography device;

a dynamic magnetic resonance imaging device; and a facial electromyography device.

9. The monitoring system in accordance with claim 1, wherein an output is set to provide a warning to the operator when the subject achieves one or more preset threshold levels of predicted brain monitor output.

10. The monitoring system in accordance with claim 1, wherein an output is coupled to an operator warning signal when the subject reaches critical levels consistent with reduced brain bloodflow.

11. The monitoring system in accordance with claim 1, wherein an is set to provide an indication of seizure activity in a pharmacologically paralyzed subject as would occur during psychiatric electroconvulsive therapy.

12. A patient monitoring process, comprising the steps of:

providing cardiovascular data;

providing brain monitoring data;

providing a computing device training phase by providing a trainable computer system receiving said cardiovascular data and said brain monitoring data during a training phase including analysis of said cardiovascular data said brain monitoring data collected from a same patient or precorelated data to provide a trained state or partially trained state;

providing additional cardiovascular data; and processing said additional cardiovascular data in a real-time fashion in said trained state or partially trained state to provide brain monitoring prediction data on the basis of said additional cardiovascular monitoring data without the use of said brain monitoring data and said cardiovascular data.

13. The monitoring process in accordance with claim 12, wherein said computing means training phase may occur at a slower rate than a real time processing rate to allow for input from one of a human operator and additional computer analytical tools to optimize said training phase.

14. The monitoring process in accordance with claim 12, further comprising providing event data means for providing event data, wherein said computing means training phase further includes analysis of said event data with said analysis of said cardiovascular data said brain monitoring data.

15. The monitoring process in accordance with claim 12, wherein said computing means in said trained state feeds back to a said brain monitoring means to improve noise artifact recognition by comparing predicted brain monitor output data to actual brain monitor output data.

16. The monitoring process in accordance with claim 14, wherein said event data means includes one or more of:

an expired gas concentration evaluation process for obtaining expired gas concentration data;

a drug infusion device providing drug infusion data;

input gas concentration regulation means providing input gas concentration data;

means for supplying data derived from spreadsheet type data depositories;

human operator input based on subjective and(or) objective evaluation of the subject being monitored;

expired ethanol analysis;

magnesium levels monitoring means for obtaining magnesium therapy monitoring data;

specific drug or alcohol blood level monitoring means to provide drug/alchohol blood level data;

a standard skin galvanic resistance lie detector for providing galvaning lie detector resistance data;

a meditation state source data indicating achieved states of meditation;

means for monitoring specific events during surgery and providing surgery event data;

g-force measurement means for providing g-force data within an aircraft, spacecraft, and(or) flight simulator; and means for providing psychometric performance data based on answers to questions and(or) performance of specific tasks.

17. The monitoring process in accordance with claim 12, wherein said training phase can continue beyond an initial training period wherein said brain monitoring prediction data is provided on the basis of said cardiovascular monitoring data without the use of said brain monitoring data after said initial training period.

18. The monitoring process in accordance with claim 12, wherein said cardiovascular monitoring data is obtained from one or more of:

a thoracic bioimpedance monitoring means;

a modified thoracic bioimpedance monitoring means that concomitantly utilizes electrodes positioned on the subject and used for electrocardiographic analysis;

a heart rate variability real-time series analysis device;

a electrocardiographic morphology analysis device operating in real time and producing interpretive data;

a electrocardiographic real-time Fourier-type spectral waveform analysis device with or without producing interpretive data;

a real-time electrocardiographic interpretive arrhythmia waveform analysis device;

a real-time interpretive electrocardiographic ischemic waveform analysis device;

a noninvasive plethysmographic or doppler peripheral pulse waveform data gathering device;

invasive waveform and(or) pressure data means gathering data from the systemic arterial system, pulmonary arterial system, occluded pulmonary arterial system, and cardiac chambers;

a device for providing continuous thermodilution cardiac output data from invasive catheter(s);

means for providing continuous mixed venous oxygen hemoglobin saturation data; and means for supplying echocardiographic data in one, two, or three dimensions.

19. The monitoring process in accordance with claim 12, wherein said brain monitoring data is obtained from one or more of:

a full multiple lead electroencephalography device;

full multiple lead electroencephalography device with individual Fourier wave analysis in real time of every channel;

a processed EEG resulting in data comprising complex graphical or numeric output, simplified graphical or numeric output, and(or) a simple scaled numerical value correlating with general cerebral unilateral or bilateral cortical activity;

an evoked potential measurement means from somatosensory evoked potentials, brainstem auditory evoked potentials, visual evoked potentials, and(or) motor evoked potentials;

a positron emission tomography device;

a dynamic magnetic resonance imaging device; and a facial electromyography device.

20. The monitoring process in accordance with claim 12, wherein an output is set to provide a warning to the operator when the subject achieves one or more preset threshold levels of predicted brain monitor output.

* * * * *